(12) United States Patent
Sreenivasan et al.

(10) Patent No.: US 12,002,578 B2
(45) Date of Patent: Jun. 4, 2024

(54) SYSTEMS AND METHODS FOR AUGMENTED REALITY-ENHANCED FIELD SERVICES SUPPORT

(71) Applicant: KONINKLIJKE PHILIPS N.V., Eindhoven (NL)

(72) Inventors: Rithesh Sreenivasan, Bangalore (IN); Oladimeji Feyisetan Farri, Yorktown Heights, NY (US); Sheikh Sadid Al Hasan, Cambridge, MA (US); Tilak Raj Arora, Gurgaon (IN); Vivek Varma Datla, Ashland, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 17/292,467

(22) PCT Filed: Dec. 2, 2019

(86) PCT No.: PCT/EP2019/083207
§ 371 (c)(1),
(2) Date: May 10, 2021

(87) PCT Pub. No.: WO2020/120180
PCT Pub. Date: Jun. 18, 2020

(65) Prior Publication Data
US 2022/0020482 A1    Jan. 20, 2022

Related U.S. Application Data

(60) Provisional application No. 62/777,278, filed on Dec. 10, 2018.

(51) Int. Cl.
*G16H 40/63* (2018.01)
*G02B 27/01* (2006.01)
*G06F 3/16* (2006.01)
*G06N 3/04* (2023.01)
*G16H 30/40* (2018.01)

(52) U.S. Cl.
CPC .......... *G16H 40/63* (2018.01); *G02B 27/017* (2013.01); *G06F 3/167* (2013.01); *G06N 3/04* (2013.01);
(Continued)

(58) Field of Classification Search
CPC ........ G16H 40/63; G16H 30/40; G16H 40/40; G02B 27/017; G02B 2027/014; G06F 3/167; G06F 3/011; G06N 3/04
(Continued)

(56) References Cited

U.S. PATENT DOCUMENTS

2002/0069072 A1* 6/2002 Friedrich ......... G05B 19/41875
704/275
2013/0010068 A1* 1/2013 Tiernan ................ G06V 30/142
348/46
(Continued)

FOREIGN PATENT DOCUMENTS

CN    106096857        11/2016
EP    2942717 A1 * 11/2015 ............. G01C 21/36

OTHER PUBLICATIONS

Mobiliya, "Augmented Reality for Equipment Maintenance | Training | Sales", 2016 (Year: 2016).*
(Continued)

*Primary Examiner* — Joy Chng (57) ABSTRACT

An augmented reality (AR) content generation method includes: acquiring, with a camera of an AR device, one or more images of a component of a medical imaging or medical therapy device; receiving, from a microphone of the AR device, a triggering audio segment; generating one or more query data structures from both the one or more images and the triggering audio segment; retrieving AR instructional content related to the medical imaging or medical therapy device matching the generated one or more query
(Continued)

data structures from a database; and outputting the AR instructional content one or more of (i) displayed superimposed on video displayed by the AR device and/or (ii) displayed on a head mounted display of the AR device and/or (iii) as audio content via a loudspeaker of the AR device.

19 Claims, 4 Drawing Sheets

(52) U.S. Cl.
CPC ....... *G16H 30/40* (2018.01); *G02B 2027/014* (2013.01)

(58) Field of Classification Search
USPC ......................................................... 705/2–3
See application file for complete search history.

(56) References Cited

U.S. PATENT DOCUMENTS

| | | | |
|---|---|---|---|
| 2013/0100685 A1 | 4/2013 | Weekamp | |
| 2014/0310595 A1* | 10/2014 | Acharya | G06F 3/011 715/706 |
| 2014/0341528 A1* | 11/2014 | Mahate | H04N 5/91 386/224 |
| 2015/0325047 A1* | 11/2015 | Conner | G06F 3/04847 345/633 |
| 2016/0173816 A1* | 6/2016 | Huenerfauth | G16H 40/40 348/14.02 |
| 2017/0083671 A1* | 3/2017 | Benner | G06Q 10/20 |
| 2017/0230675 A1* | 8/2017 | Wierstra | G06N 3/047 |
| 2019/0183576 A1* | 6/2019 | Fahim | A61B 34/10 |

OTHER PUBLICATIONS

Shaham, Augmented Reality Instruction Manual: the Perfect User Manual?, Jul. 3, 2018, TechSee, https://techsee.me/blog/augmented-reality-instruction-manual/ (Year: 2018).*

International Search Report and Written Opinion dated Feb. 4, 2020 for International Application No. PCT/EP2019/083207 Filed Dec. 2, 2019.

Ramakrishn, et al: "An AR Inspection Framework: Feasibility Study with Multiple AR Devices", 2016 IEEE International Symposium on Mixed and Augmented Reality Adjunct Proceedings.

Mobiliya, "Augmented Reality for Equipment Maintenance | Training | Sales", 2016.

* cited by examiner

SYSTEMS AND METHODS FOR AUGMENTED REALITY-ENHANCED FIELD SERVICES SUPPORT

CROSS REFERENCE TO RELATED APPLICATIONS

This application is the U.S. National Phase application under 35 U.S.C. § 371 of International Application No. PCT/EP2019/083207 filed Dec. 2, 2019, which claims the benefit of U.S. Provisional Patent Application No. 62/777,278 filed Dec. 10, 2018. These applications are hereby incorporated by reference herein.

FIELD

The following relates generally to the field servicing arts and more particularly to the medical imaging device and system servicing arts, to the augmented vision arts, and to related arts.

BACKGROUND

Medical imaging devices include very complex systems such as magnetic resonance imaging (MRI) devices, transmission computed tomography (CT) imaging devices, emission imaging systems such as positron emission tomography (PET) imaging devices and gamma cameras for single photon emission computed tomography (SPECT) imaging, hybrid systems that provide multiple modalities in a single device, e.g. a PET/CT or SPECT/CT imaging device, and imaging devices designed for guiding biopsies or other interventional medical procedures, commonly referred to as image guided therapy (iGT) devices. These are merely illustrative examples.

Modern medical imaging devices and systems present unusual challenges from a maintenance standpoint. They typically include a large number of sub-systems for widely varying purposes, including for example: mechanical and electromechanical systems for loading a patient, transport into the imaging examination area, and subsequent unloading; an x-ray tube assembly and x-ray detector array in the case of a CT imaging device; a rotating gantry assembly again in the case of CT; annular rings of radiation detector modules in the case of a PET imaging device; radiation detector heads and associated robotic hardware for maneuvering the heads around a patient in the case of a gamma camera; a superconducting magnet and associated liquid helium tank and/or other cryostat hardware in the case of MRI; user interfacing components such as computerized controllers, control buttons, switches, touch-sensitive displays, and the like; and so forth. Servicing of medical imaging devices usually must be performed in the field, that is, at the hospital or other medical facility at which the medical imaging device is deployed. Moreover, it is highly desirable to minimize servicing downtime since hospitals and other medical facilities expect these devices to be available nearly continuously to provide imaging or image-guided therapy to patients.

Yet a further difficulty from a servicing standpoint is that medical imaging devices are usually under near-constant development by the manufacturer, and are marketed with various optional components and component packages, so that different deployed installations of the same make/model of medical imaging device may nonetheless have different components depending upon when they were manufactured and depending upon which options the customer chose to purchase.

Most medical equipment users expect constant customer support and service availability with minimal machine down-time. Equipment manufacturers can benefit from technologies and platforms that will enable them to offer support and services to their customers better and faster. This would result in increased customer satisfaction. From the healthcare perspective any downtime is critical as the system is already overloaded. Efficient field service results in higher productivity, reduced downtime and improved customer satisfaction.

Field service engineers (FSE) in the health care industry may have a wide range of field expertise and widely varying familiarity within the pool of FSEs with certain medical devices. If the particular FSE sent on a particular service call has limited familiarity with the particular medical imaging system under service, this can have a negative impact on the effectiveness of support the FSE can provide to the customer, which in turn can lead to customer dissatisfaction. The FSE operating at the customer location may also have minimal (or no) pauses in his/her workflow and minimal resources to review/search for the best approach to address an issue.

The following discloses a new and improved systems and methods.

SUMMARY

In one disclosed aspect, a non-transitory computer-readable medium stores instructions readable and executable by at least one electronic processor to perform an augmented reality (AR) content generation method. The method includes: acquiring, with a camera of an AR device, one or more images of a component of a medical imaging or medical therapy device; receiving, from a microphone of the AR device, a triggering audio segment; generating one or more query data structures from both the one or more images and the triggering audio segment; retrieving AR instructional content related to the medical imaging or medical therapy device matching the generated one or more query data structures from a database; and outputting the AR instructional content one or more of (i) displayed superimposed on video displayed by the AR device and/or (ii) displayed on a head mounted display of the AR device and/or (iii) as audio content via a loudspeaker of the AR device.

In another disclosed aspect, an augmented reality (AR) content generation system includes an AR device including a camera, a microphone, a display, and a loudspeaker. The camera is configured to acquire one or more images of a component of a medical imaging or medical therapy device. At least one electronic processor is programmed to: receive, from the microphone, a triggering audio segment; generate one or more query data structures from both the one or more images and the triggering audio segment; retrieve AR instructional content related to the medical imaging or medical therapy device matching the generated one or more query data structures from a database; and output the AR instructional content one or more of (i) displayed superimposed on video displayed by the AR device and/or (ii) displayed on a head mounted display of the AR device and/or (iii) as audio content via the loudspeaker.

In another disclosed aspect, an augmented reality (AR) content generation method includes: acquiring, with a camera of an AR device, one or more images of a component of a medical imaging or medical therapy device; receiving, from a microphone of the AR device, a triggering audio segment; generating one or more query data structures from both the one or more images and the triggering audio segment by processing the one or more images using a convolutional neural network (CNN) and processing the triggering audio segment using a recurrent neural network (RNN); retrieving AR instructional content matching the generated one or more query data structures from a database; and outputting the AR instructional content one or more of (i) displayed superimposed on video displayed by the AR device and/or (ii) displayed on a head mounted display of the AR device and/or (iii) as audio content via a loudspeaker of the AR device, the visual instructions including one or more of a relevant section of a service manual related to the component and annotations from the service manual related to the component.

One advantage resides in providing real-time automated assistance for service personnel.

Another advantage resides in providing real-time automated retrieval of augmented reality (AR) content for service personnel.

Another advantage resides in providing real-time automated retrieval and presentation of AR content to assist in a service call which is presented from the point-of-view of the service person and is tightly integrated with the service operations to be performed.

Another advantage resides in providing real-time AR content leveraging a real-time video and/or audio feed to automatically identify and retrieve appropriate AR content.

Another advantage resides in outputting real-time AR content on a head mounted display of an AR device or as audio content via a loudspeaker of the AR device.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

The following generally relates to providing AR support for FSEs (or more generally, for service engineers, maintenance technicians, radiology laboratory personnel, or the like) performing maintenance of medical imaging devices.

AR content is generally not easily indexed in the same way that a printed service manual can be indexed, e.g. using a table of contents, subject page indexing system, or the like. The AR content can be multimedia content, audio content, video content, field-of-view schematic overlay content, and so forth, which is not readily amenable to indexing. AR content for assisting in medical imaging device servicing could be variously indexed, e.g. by part, module, task, and/or so forth. Even with a printed service manual, the content may be found at different places in different manuals, for example relevant content for servicing part X may be found indexed under part Y if it is necessary to remove part Y in order to access part X. Moreover, even if the service engineer knows which content is needed, it may be time consuming to drill down through a hierarchical index of service manuals to locate the relevant content. With multimedia content such index searching is particularly problematic, as one cannot necessarily simply flip to the specific service manual page cited in the index. Particularly so for servicing medical imaging devices, which can comprise tens of thousands of interrelated parts and commensurate numbers of modules, service tasks, and so forth.

In embodiments disclosed herein, an automated approach is provided for identifying and retrieving AR content for presentation. A user asks the system for help using a suitable keyword or key-phrase (sometimes referred to herein as a triggering audio segment) while looking at the part/module under service through AR glasses, an AR headset, or the like; or while pointing the camera of a mobile device at the part/module under service to acquire video of it. One or more query images are captured by the AR glasses, mobile device camera, or other similar device, and query text is generated by a microphone with transcription, for example extracting the triggering audio segment from the audio component of audio/video being recorded by the AR glasses or mobile device camera/microphone setup. The images/text are formulated into a joint image/text query vector. These operations are performed at the customer site, for example by a FSE during a service call.

Offline (that is, sometime before the service call), images from the service manuals and associated text (e.g. figure captions) are translated into joint image/text AR content vectors for indexing the AR content. The AR content vectors are produced using the same vector formulation procedure that is used to generate the query vector. Identifying relevant AR content is then done by comparing the query vector with the database of AR content vectors. One or more candidate AR content vectors are thus identified, and the corresponding AR content is retrieved (or, in some embodiments, reconstructed from the AR content vector by decoding using an autoencoder).

In embodiments disclosed herein, the vector elements are derived from the image and text content using neural networks. Particularly, a Convolutional Neural Network (CNN) is used to derive vector elements from image content, while a Recurrent Neural Network (RNN) is used to derive vector elements from text content. The triggering keyword or key-phrase serves as an attention mechanism for triggering the RNN, and informative text content (e.g. names of parts or modules, named symptoms, or so forth) are emphasized in the generation of vector elements. While some embodiments are expected to be efficient and effective, other approaches for deriving vector elements representative of image and text content may alternatively be used. In one other illustrative contemplated embodiment, a single CNN may process both the image and text content to generate the joint image/text vector.

For the vector matching, a cosine similarity metric is employed in an illustrative embodiment, but more generally another vector similarity metric may be used, such as a Euclidean distance or other vector distance metric.

Using both real time images and real time text can be more effective for accurately identifying AR content versus images alone. In some embodiments disclosed herein, the AR content is reconstructed from the representative joint image/text vector representing the AR content using an autoencoder; however, alternatively the vector could be linked to corresponding stored AR content that is then retrieved. The retrieved (and optionally decoded or reconstructed) AR content may be variously presented, e.g. by displaying the service manual images (or, in a more advanced embodiment, by superimposing annotations derived from those images onto real-time video observed by the AR device), and by displaying associated text of the manual and/or using text-to-speech to convey the textual content audibly.

It should be noted that the use of a vector as the data structure for formatting the query and the AR content for comparison with the query is merely illustrative. More generally, the query and the comparative AR content can be formatted using any chosen data structure, such as a one-dimensional vector, or a two-dimensional matrix, or a three-dimensional or higher-dimensional matrix, or a set of vectors of different lengths, or so forth. The illustrative examples employing a single vector for formulating the query and comparative AR content can have certain processing advantages as such a vector may be more easily input to a neural network designed to receive a single vector as input, but more generally any type of data structure could be used in place of the illustrative vectors.

In embodiments disclosed herein, AR glasses (e.g. Google glasses) are employed as the user interface for acquiring images and audio and for presenting the AR content. In a variant embodiment, a mobile device (cellphone or tablet computer) may serve as the user interface. In this case, the real-time query images may be obtained using the built-in camera, and AR content may be displayed on the mobile device display and/or as annotations superimposed on real-time video captured by the built-in camera of the mobile device.

The training data for training the vector extraction (e.g. CNN and RNN) and (optional) autoencoder may be obtained from the training manuals (possibly with some manual segmentation/delineation of sections or so forth) and/or by having a user look at the relevant part/module through AR glasses while speaking appropriate typical query verbiage. The images are preferably acquired at different viewing angles, lighting angles, illumination levels, or so forth, and/or such variant images may be synthesized using appropriate image processing techniques (e.g. by adjusting the image contrast curve to simulate different lighting conditions). Similarly, the audio content can be generated by speakers with different accents, voice pitches, or so forth, and/or these may be simulated by audio processing to perform pitch adjustment et cetera. Manual annotation of training data may also be performed, such as manually delineating bounding boxes around key features in the training images. Ground truth labeling for supervised training may be obtained from the manuals (e.g., if the manual positively identifies part numbers or so forth) and/or by manual labeling of images/audio.

The following generally discloses AR based field services support. In general, the FSE (or more generally, service engineer, maintenance technician, radiology laboratory staffer, or the like) is provided with AR glasses which can capture real time video and audio. The system processes the audio and video and attempts to match the transformed pixels and text with the indexed instructions and images within service manuals for the medical device/equipment being reviewed for a fault. A medical device service manual is initially pre-processed by tokenizing and parsing the text, plus segmenting the images and mapping the parts identified in the images to corresponding labels noted in the document. Using either a top-down (image features represented by a CNN, and an attention mechanism and a RNN represents the labels associated with certain regions in the image) or a bottom-up approach (CNN-based selection of important regions in the images and soft max classification of labels for these regions), the system is able to index all image-text links existing in the service manual. This makes up a service manual pre-processing module, in this example.

A search model leverages (a) a speech-to-text model that converts the incoming/input audio signals from the AR glasses into word sequences; (b) the pre-processing module to generate a joint vector representation of the resulting text and the videos/images captured by the AR glasses; and (c) an algorithm that tries to match the input image and text vector to the appropriate image-text link from the already indexed service manual.

If there is a matching image-text link, the image and text/instructions are reconstructed using an autoencoder architecture trained on all the image-text links from the service manual such that the FSE could experience a visually similar image (compared to current on-device environment) along with easily interpretable instruction sets to resolve the existing issue. This can be achieved by adding a few constraints into the decoding part of the model based on some pre-defined loss functions that would ensure generation of image/s capturing on-device visual characteristics of the problem as well as easy to comprehend instruction sets, given a matched image-text pair from the service manual. The reconstructed image and instructions are then displayed in the visual field of the AR glasses for the FSE. If there is no matching image-text link, the search pipeline suggests the top 2 closest image-text links. After reconstruction by the autoencoder model, only the images are displayed to the FSE in the AR field of view. The FSE then selects by speaking ("I choose Image A") or 'touching' the best choice, and the corresponding instructions would be displayed. In this example the retrieved content is decoded (i.e. reconstructed) using an autoencoder. In other contemplated embodiments, the original AR content is stored and indexed by the image-text links of the already indexed service manual, in which case no reconstruction (i.e. no decoding) by an autoencoder or other decoding algorithm is performed.

Figure 1:
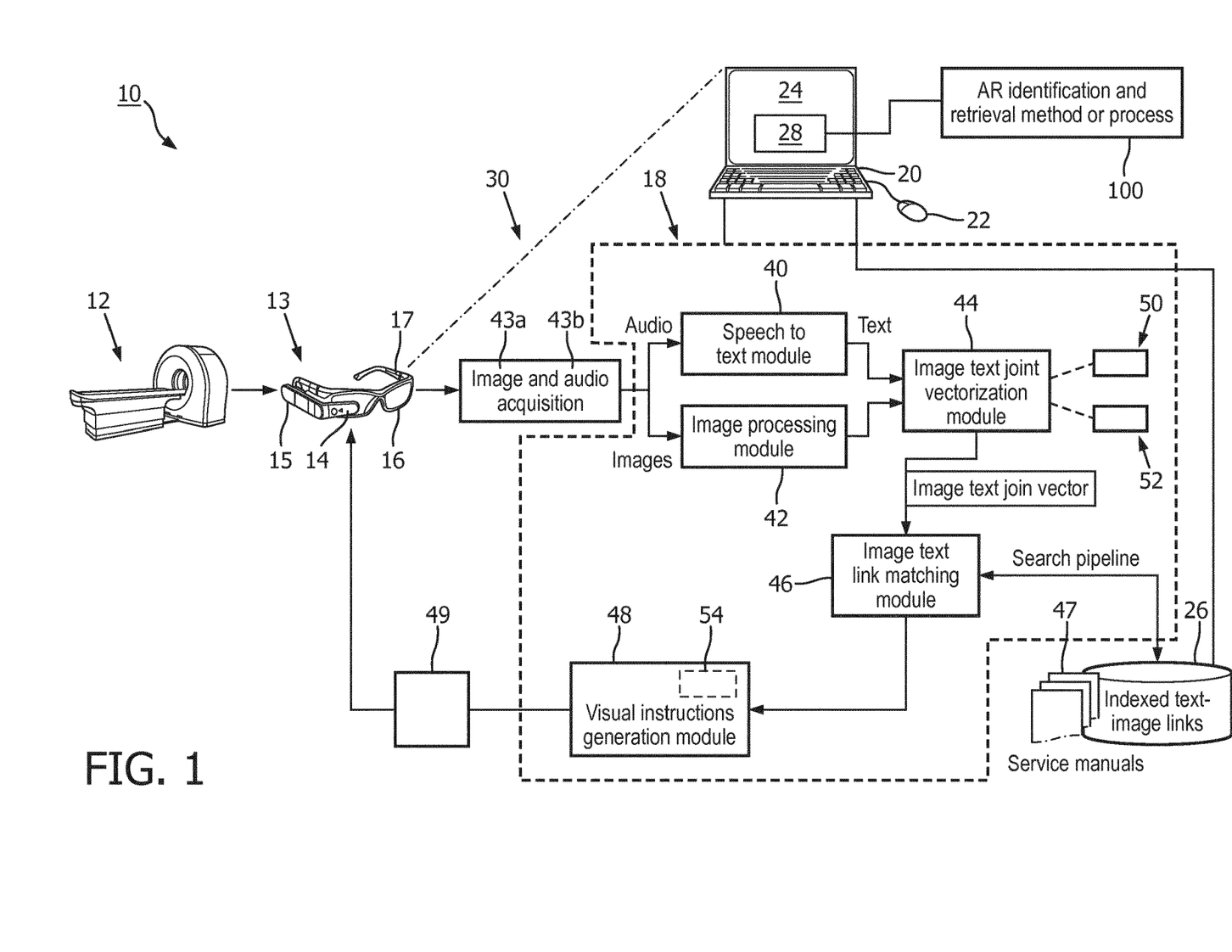
FIG. 1 diagrammatically illustrates an AR generation system according to one aspect.

With reference to FIG. 1, a system for identifying and retrieving (and optionally decoding) AR content 10 is illustrated. The system 10 is used for a service call for a medical imaging or medical therapy device 12 (shown illustratively as a PET imaging device). More generally, the medical imaging or medical therapy device 12 can be any suitable type of device, e.g. a standalone CT imaging device, a hybrid PET/CT imaging device, a magnetic resonance imaging (MRI) device, a gamma camera for single photon emission computed tomography (SPECT) imaging, an image guided therapy (iGT) device, or so forth. Even more generally, the disclosed AR based servicing guidance devices and methods may be applied to any type of system or device servicing performed in the field, e.g. may be applied to a radiation therapy delivery device, a research device such as a magnet, a cryogenic system, a factory robotic system, a processing furnace, or so forth.

The system 10 includes an AR device 13. As shown in FIG. 1, the AR device 13 can comprise a pair of AR glasses (e.g., Google Glass) worn by a FSE (or more generally, a service engineer, a maintenance technician, a radiology laboratory staffer, or the like). In another example, the AR device 13 can comprise a mobile cellphone or tablet. The AR device 13 includes a camera 14 (e.g., a stereo camera with "left-eye" and "right-eye" cameras) for acquiring images of the imaging device 12, and a microphone 15 for acquiring vocal instructions from the FSE. The AR device 13 can include a display 16 (e.g., a head-mounted display in the example of Google Glass) for visually outputting content and/or a loudspeaker 17 for audibly outputting content.

The camera 14 provides a "first person" point of view—if the AR device 13 is worn by a service person who performs (or participates in performing) the servicing then the recorded video of the service call is advantageously from the viewpoint or vantage point of the service person. By using the camera 14 the recorded video is advantageously binocular in nature and can provide depth information for extracting three-dimensional (3D) information. However, in an alternative embodiment a monocular camera is employed—in this case computer vision can generally extract 3D information based on different vantage points provided by way of natural movement of the camera (due to movement of the service person's head during servicing). As another contemplated variant, a conventional optical camera may be augmented by a range camera to provide depth information.

Generally, the AR device 13 is configured to superimpose AR content comprising one or more of image, text, audio, and the like onto either (i) a real time video acquired by the AR device (as in using a cellphone) or (ii) on a head-mounted display. In one approach, head-worn AR glasses, goggles, or the like have transparent lenses (e.g. transparent eyeglass lenses) and the display 16 is set up either at a periphery of the transparent lenses or arranged to project the displayed content onto the transparent lens or using a transparent display that makes up the lens).

A difficulty with the AR device 13 with the illustrative eyewear-mounted camera 14 is that it may provide limited support structure for mounting an electronic processor—that is, it may be difficult to integrate onto the eyeglasses a microprocessor or microcontroller with sufficient processing capacity to handle the video generation and optional processing. This is addressed in the illustrative embodiment by having the AR device 13 in wireless communication with a workstation 18 comprising a computer or other electronic data processing device with typical components, such as at least one electronic processor 20, at least one user input device (e.g., a mouse, a keyboard, a trackball, and/or the like) 22, and a display device 24. It should be noted that these components can be variously distributed. For example, the electronic processor 20 may include a local processor of a notebook computer carried by the FSE and the processor of a server computer that is accessed by the workstation terminal. In another contemplated approach, the electronic processor 20 is embodied as a cloud computing resource or other remote server computer(s) accessed by the AR device 13 via a wireless link 30, such as a 3G or 4G wireless cellular communication link, Wi-Fi link, and/or the like. The electronic processor 20 also includes or has access to one or more databases or non-transitory storage media 26 storing the AR content for supporting service operations. The non-transitory storage media 26 may, by way of non-limiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth. The display device 24 is configured to display a graphical user interface (GUI) 28 including one or more fields to receive a user input from the user input device 22.

It is to be appreciated that FIG. 1 merely shows one illustrative arrangement. As already mentioned, other types of eyewear or headwear (e.g. goggles, headband, helmet, et cetera) may serve as the support structure for the AR device 13 so as to provide a first-person view of the servicing process; additionally, as already mentioned the stereo 14 may be replaced by a camera of another type, e.g. a monocular camera, a camera-plus-range camera combination, and/or so forth. In other embodiments, the recorded video of the service call may not be from the first-person view of the service person. For example, in an alternative embodiment, the AR device comprises a mobile device (not shown) with its rear-facing camera arranged on the backside of the mobile device serving as the camera for recording the service call. In this case, the vantage will not be first-person, but the FSE can hold the mobile device to direct the rear-facing camera appropriately to record video of the part, component, or assembly for which AR content support is to be retrieved.

The system 10 is configured to perform an AR content identification and retrieval method or process 100. The non-transitory storage medium 26 stores instructions which are readable and executable by the at least one electronic processor 20 of the workstation 18 and to perform disclosed operations including performing the AR content generation method or process 100. In some examples, the method 100 may be performed at least in part by cloud processing. The instructions which are executed to perform the AR content identification and retrieval method or process 100 may be viewed as implementing: (i) a speech-to-text or a transcription module 40 and an image processing module 42 programmed to analyze images 43a captured by the camera 14 and sound 43b captured by the microphone 15 to generate corresponding text; (ii) an image-text joint vectorization module 44 programmed to generate an image-text joint vector from the text and images (as previously mentioned, more generally a data structure other than a vector is contemplated, such as a 2D, 3D, or higher-dimensional matrix, a set of vectors, and/or so forth); (iii) an image text link matching module 46 programmed to search the non-transitory storage medium 26 for relevant service manual data 47 of the medical imaging or therapy device 12 based on the image-text joint vector; and (iv) a visual instructions generation module 48 programmed to generate instructional content 49 based on the retrieved manual data and display the instructions on the display 16 of the AR device 13 (or, alternatively, audio instructions output by the loudspeaker 17 of the AR device). In some embodiments, the image-text joint vectorization module 44 can include one or more neural networks (NN) to process the images and text from the corresponding image processing module 42 and the transcription module 40. For example, the image-text joint vectorization module 44 can include a convolutional NN (CNN) 50 programmed to process one or more images captured by the camera 14, and a recurrent NN (RNN) 52 programmed to process a triggering audio segment (i.e., sound) captured by the microphone 15. In other embodiments, the visual instructions generation module 48 can include an autoencoder 54 programmed to reconstruct the visual (or audio) instructions.

Figure 2:
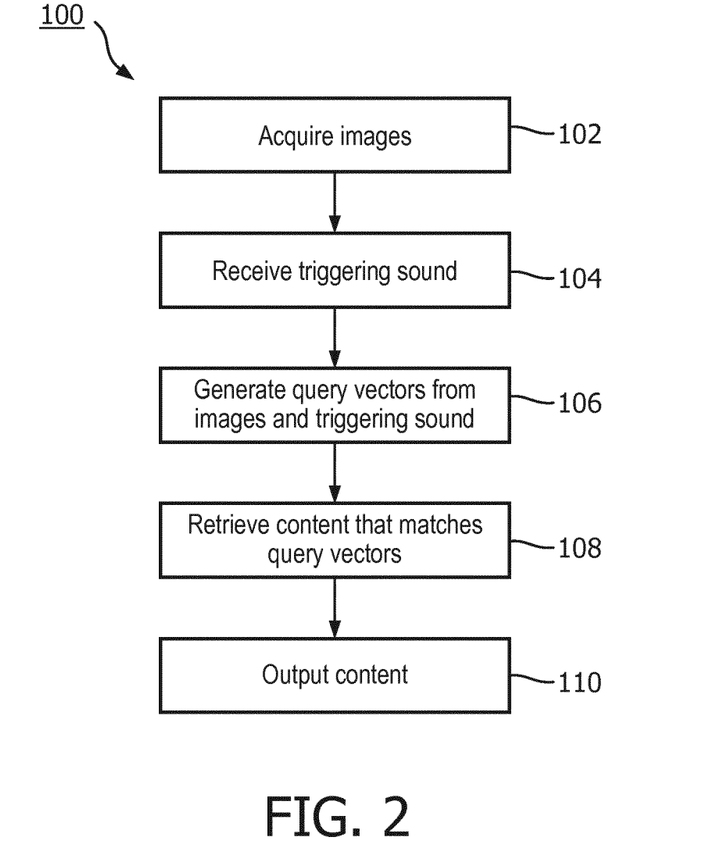
FIG. 2 shows exemplary flow chart operations of the system of FIG. 1.

With reference to FIG. 2, an illustrative embodiment of the AR content generation method 100 is diagrammatically shown as a flowchart. The method 100 can be executed by the at least one electronic processor 20 of the workstation 18. At 102, one or more images of a component of the medical imaging or medical therapy device 12 are acquired with the camera 14 of the AR device 13. At 104, a triggering audio segment is received from the microphone 15 of the AR device 13.

At 106, one or more query vectors are generated from both the one or more images and the triggering audio segment. In some embodiments, another vector similarity metric may be used, such as a Euclidean distance or other vector distance metric. In one example, the images are processed with a NN, for example the CNN 50. In another example, the triggering audio segment is processed with a NN, for example the RNN 52.

At 108, AR instructional content that matches the generated query vectors is retrieved from a database (e.g., the non-transitory storage medium 26). To do so, a cosine similarity metric is used to match the generated query vectors with the AR instructional content. In one embodiment, content of the database 26 is indexed by index vectors generated using a same process as is used in generating the one or more query vectors. The matching includes matching the one or more query vectors with the index vectors indexing the retrieved AR instructional content. In another embodiment, content of the database 26 is encoded as vectors using a same process as is used in generating the one or more query vectors. The retrieving then includes retrieving encoded AR instructional content from the database 26, and decoding the encoded AR instructional content with an auto encoder 54.

At 110, the AR instructional content is output as one or more of (i) displayed superimposed on video displayed by the display 16 of the AR device 13 (e.g., when the AR device comprises a cellular telephone or electronic tablet) and/or (ii) displayed on a head mounted display 16 of the AR device (e.g., when the AR device comprises Google glasses) and/or (iii) as audio content via the loudspeaker 17 of the AR device. In one example, the visual instructions are output as a relevant section of a service manual related to the component. In another example, the visual instructions are output as annotations from the service manual related to the component.

Figure 3:
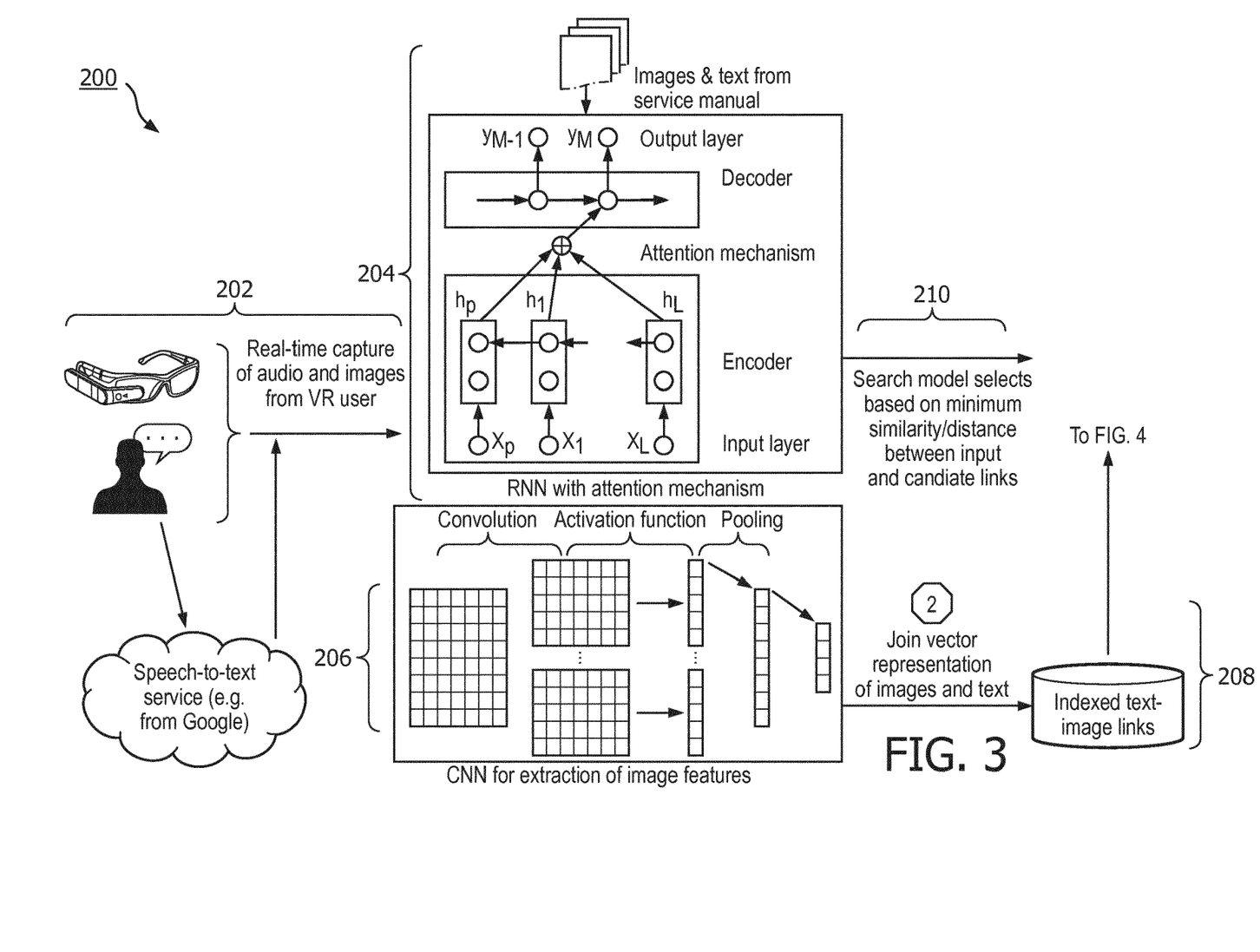
FIGS. 3 and 4 show exemplary flow chart operations of the method of FIG. 2.

With reference to FIG. 3, an illustrative embodiment of the operation 106 of FIG. 2 (e.g., performed by the image text joint vectorization module 44 of FIG. 1) is diagrammatically shown. At 202, images 43*b* are captured by the camera 14 and/or text is generated by voice recognition processing of the audio 43*a* captured by the microphone 15, respectively, of the AR device 13. At 204, the acquired text 43*b*, along with text from the service data manual data 47, are input to the RNN 52 and processed. At 206, the acquired images 43*a*, along with images from the service data manual data 47, are input to the CNN 50 and processed. At 208, one or more query vectors (i.e., joint-image-text vectors) is generated from the processing of the CNN 50 and the RNN 52. At 210, the database 26 is indexed to find and select instructional content 49 which has a minimum similarity distance from the query vectors.

Figure 4:
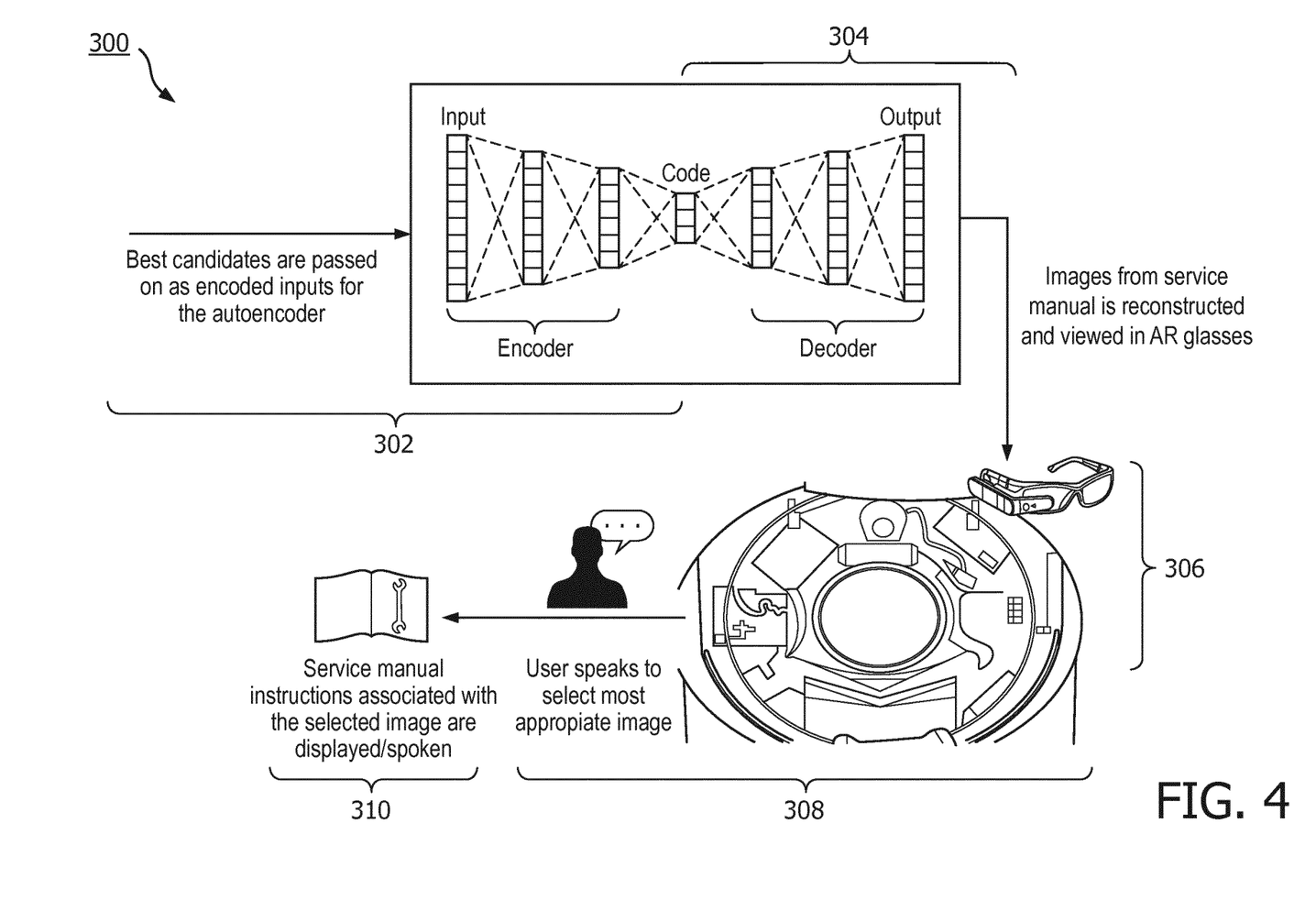

With reference to FIG. 4, an illustrative embodiment of the operation 108 of FIG. 2 (e.g., performed by the link matching module 46 of FIG. 1) is diagrammatically shown. At 302, the instructional content 49 is input to the autoencoder 54. At 304, the instructional content 49 is decoded to generate reconstructed images from the service manual data 47. At 306, the images are displayed on the display 16 of the AR device 13. At 308, the microphone 15 of the AR device 13 receives a triggering sound indicative of a selection of one of the displayed images. At 310, service manual data 47 associated with the selected image is displayed on the display 16 (or, additionally or alternatively, output with the loudspeaker 17).

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A non-transitory computer-readable medium storing instructions readable and executable by at least one electronic processor to perform an augmented reality (AR) content generation method, the method comprising:
   acquiring, with a camera of an AR device, one or more images of a component of a medical imaging or medical therapy device;
   processing the acquired one or more images with an image processor to generate one or more processed images;
   receiving, from a microphone of the AR device, a triggering audio segment;
   processing the received triggering audio segment with a speech-to-text process or a transcription process to generate a processed triggering audio segment;
   generating one or more query vectors from both the one or more processed images and the processed triggering audio segment;
   retrieving AR instructional content related to the medical imaging or medical therapy device matching the generated one or more query vectors from a database; and
   outputting the AR instructional content one or more of (i) displayed superimposed on video displayed by the AR device and/or (ii) displayed on a head mounted display of the AR device and/or (iii) as audio content via a loudspeaker of the AR device.

2. The non-transitory computer-readable medium of claim 1 wherein the outputting includes one of:
   displaying the AR instructional content superimposed on video displayed by the AR device comprising a cellular telephone or electronic tablet; or
   displaying the AR instructional content superimposed on a head mounted display of the AR device.

3. The non-transitory computer-readable medium of claim 1, wherein content of the database is indexed by index data structures generated using a same process as is used in generating the one or more query vectors, and
   the matching comprises matching the one or more query vectors with the index data structures indexing the retrieved AR instructional content.

4. The non-transitory computer-readable medium of claim 1, wherein content of the database is encoded as vectors using a same process as is used in generating the one or more query vectors, and the retrieving includes:
   retrieving encoded AR instructional content from the database; and
   decoding the encoded AR instructional content with an auto encoder.

5. The non-transitory computer-readable medium of claim 1, wherein the generating of the one or more query vectors data structures includes:
   processing the one or more images using a neural network (NN).

6. The non-transitory computer-readable medium of claim 5, wherein the NN processing the one or more images is a convolutional NN.

7. The non-transitory computer-readable medium of claim 1, wherein the generating of the one or more query vectors includes:
   processing the triggering audio segment using a neural network (NN).

8. The non-transitory computer-readable medium of claim 7, wherein the NN processing the triggering audio segment is a recurrent NN.

9. The non-transitory computer-readable medium of claim 1, wherein the retrieving uses a cosine similarity metric to match the generated one or more query vectors with the AR instructional content.

10. The non-transitory computer-readable medium of claim 1, wherein outputting the visual instructions further includes one or more of:
   outputting a relevant section of a service manual related to the component;
   outputting annotations from the service manual related to the component.

11. An augmented reality (AR) content generation system, comprising:
   an AR device including a camera, a microphone, a display, and a loudspeaker, the camera being configured to acquire one or more images of a component of a medical imaging or medical therapy device;
   at least one electronic processor programmed to:
   process the acquired one or more images with an image processor to generate one or more processed images;
   receive, from the microphone, a triggering audio segment;
   process the received triggering audio segment with a speech-to-text process or a transcription process to generate a processed triggering audio segment generate one or more query vectors from both the one or more processed images and the processed triggering audio segment;
   retrieve AR instructional content related to the medical imaging or medical therapy device matching the generated one or more query vectors from a database; and
   output the AR instructional content one or more of (i) displayed superimposed on video displayed by the AR device and/or (ii) displayed on a head mounted display of the AR device and/or (iii) as audio content via the loudspeaker.

12. The system of claim 11, wherein the at least one electronic processor is programmed to:
   index content of the database by index vectors generated using a same process as is used in generating the one or more query vectors, and
   matching the one or more query vectors with the index vectors indexing the retrieved AR instructional content.

13. The system of claim 11, wherein the at least one electronic processor is programmed to:
   encode content of the database as vectors using a same process as is used in generating the one or more query vectors,
   retrieve encoded AR instructional content from the database; and
   decode the encoded AR instructional content with an auto encoder.

14. The system of claim 11, wherein the at least one electronic processor is programmed to:
   generate the one or more query vectors by processing the one or more images using a convolutional neural network (CNN).

15. The system of claim 11, wherein the at least one electronic processor is programmed to:
   generate the one or more query vectors by processing the triggering audio segment using a recurrent neural network (RNN).

16. The system of claim 11, wherein the at least one electronic processor is programmed to:
   retrieve the AR instructional content with a cosine similarity metric to match the generated one or more query vectors with the AR instructional content.

17. The system of claim 11, wherein the at least one electronic processor is programmed to output the visual instructions by one or more of:
   outputting a relevant section of a service manual related to the component;
   outputting annotations from the service manual related to the component.

18. An augmented reality (AR) content generation method, comprising:
   acquiring, with a camera of an AR device, one or more images of a component of a medical imaging or medical therapy device;
   receiving, from a microphone of the AR device, a triggering audio segment;
   identifying AR instructional content related to the medical imaging or medical therapy device in a database using both the one or more images of the component of the medical imaging or medical therapy device and the triggering audio segment;
   retrieving the identified AR instructional content from the database; and
   outputting the retrieved AR instructional content one or more of (i) displayed superimposed on video displayed by the AR device and/or (ii) displayed on a head mounted display of the AR device and/or (iii) as audio content via a loudspeaker of the AR device, the visual instructions including one or more of a relevant section of a service manual related to the component and annotations from the service manual related to the component.

19. The method of claim 18, wherein the identifying of the AR instructional content includes:
   generating a joint vector representation of the one or more images of the component of the medical imaging or medical therapy device and the triggering audio segment, and
   matching the structures joint vector representation with index vectors indexing AR instructional content of the database.

* * * * *